US00PP18142P2

(12) United States Plant Patent
Hensler

(10) Patent No.: US PP18,142 P2
(45) Date of Patent: Oct. 23, 2007

(54) ***VERONICA* PLANT NAMED 'CHRISTY'**

(50) Latin Name: *Veronica×hybrida*
Varietal Denomination: CHRISTY

(76) Inventor: Christy Ann Hensler, 952 Viet Rd., Newport, WA (US) 99156

( * ) Notice: Subject to any disclaimer, the term of this patent is extended or adjusted under 35 U.S.C. 154(b) by 23 days.

(21) Appl. No.: 11/441,670

(22) Filed: May 25, 2006

(51) Int. Cl.
*A01H 5/00* (2006.01)

(52) U.S. Cl. ..... Plt./251

(58) Field of Classification Search ..... Plt./251
See application file for complete search history.

*Primary Examiner*—Kent Bell
*Assistant Examiner*—Annette H Para

(57) ABSTRACT

A new cultivar of *Veronica* plant named 'CHRISTY' that is characterized by low spreading habit, violet-blue flowers, and soft green fern-like foliage. In combination these traits set 'CHRISTY' apart from all other existing varieties of *Veronica* known to the inventor.

3 Drawing Sheets

Genus: *Veronica*. Species:×*hybrida*.
Denomination: 'CHRISTY'.

BACKGROUND OF THE INVENTION

The present invention relates to a new and distinct cultivar of speedwell plant grown as an ornamental for use in border, rock garden, and as a groundcover for the landscape. The new variety is known botanically as *Veronica×hybrida* and will be referred to hereinafter by the cultivar name 'CHRISTY'.

'CHRISTY' is a hybrid plant which resulted from the open cross-pollination of an individual *Veronica austriaca* 'Crater Lake Blue' (unpatented) as the female parent, and an unnamed individual *Veronica prostrata* (unpatented) as the male parent. Cross-pollination was carried out by the inventor, at the inventor's nursery in Newport, Wash.

The inventor began experimenting with inter-specific hybrids of *Veronica* in 1992. The initial intention of this cross was not to make a selection, but to determine if the cross would be successful, or even possible. Two methods of deliberate cross-pollination were utilized. In 1994 the inventor bound together blooming sprigs from the pollen parent and used them as a "pollen broom" to brush over the flowers of the seed parent, and disperse pollen to fertilize the flowers. The other method utilized by the inventor in 1994 to transfer pollen was honeybees. During and following both crosses the parents were kept under cover and apart from other nursery stock, in an area left bare for dehiscence of the seed. Successful cross-pollination resulted, producing seed, which was then sown by the inventor. The seedling 'CHRISTY' grew from this seed batch and was selected by the inventor in 1996.

The new *Veronica* variety named 'CHRISTY' exhibits low spreading habit, soft green fern-like leaves, and violet-blue flowers. 'CHRISTY' reaches 20 cm. in height, and 40 cm. in width at maturity. Cultural requirements well-draining soil, full sun and adequate but not excess water. 'CHRISTY' is not susceptible or resistant to any pest or disease known to the inventor.

'CHRISTY' is distinguishable from the female parent by leaf margin, low spreading habit and late spring through summer blooming. The female parent *Veronica austriaca* 'Crater Lake Blue' exhibits tall upright shrub-like habit and blooms in late summer. 'CHRISTY' is distinguishable from the male parent by leaf margin, low spreading habit and late spring through summer blooming. The male parent *Veronica prostrata* exhibits low creeping habit and blooms in early summer. The leaf margin of 'CHRISTY' is sharply cleft in comparison to both parents.

'CHRISTY' was first asexually propagated in 1996 using the method of division. Asexual propagation was conducted by the inventor, at the inventor's nursery in Newport, Wash. Since that time under careful observation, 'CHRISTY' has been determined stable, uniform, and reproduces true to type in successive generations of asexual propagation.

SUMMARY OF THE INVENTION

The following traits have been repeatedly observed and represent the distinguishing characteristics of the new *Veronica* variety known as 'CHRISTY.' These traits in combination distinguish 'CHRISTY' from all other existing varieties of *Veronica* known to the inventor. 'CHRISTY' has not been tested under all possible conditions and phenotypic differences may be observed with variations in environmental, climatic, and cultural conditions, however, without any variance in genotype. Growing requirements are similar to the species.

1. 'CHRISTY' exhibits low spreading habit.
2. 'CHRISTY' exhibits soft green fern-like foliage.
3. 'CHRISTY' exhibits violet-blue flowers.
4. 'CHRISTY' is an ornamental grown for use in border, rock garden and, as a groundcover for the landscape.
5. 'CHRISTY' is asexually propagated by the methods of division and softwood cuttings.
6. 'CHRISTY' reaches 20 cm. in height and 40 cm. in width at maturity.
7. 'CHRISTY' blooms profusely from late spring through summer.
8. 'CHRISTY' is hardy to USDA Zone 3.

BRIEF DESCRIPTION OF THE DRAWINGS

The accompanying color drawings illustrate the overall appearance of the new *Veronica* variety named 'CHRISTY' showing colors as true as it is reasonably possible to obtain in colored reproductions of this type.

The drawing labeled

The drawing labeled

The drawing labeled

Figure 1:
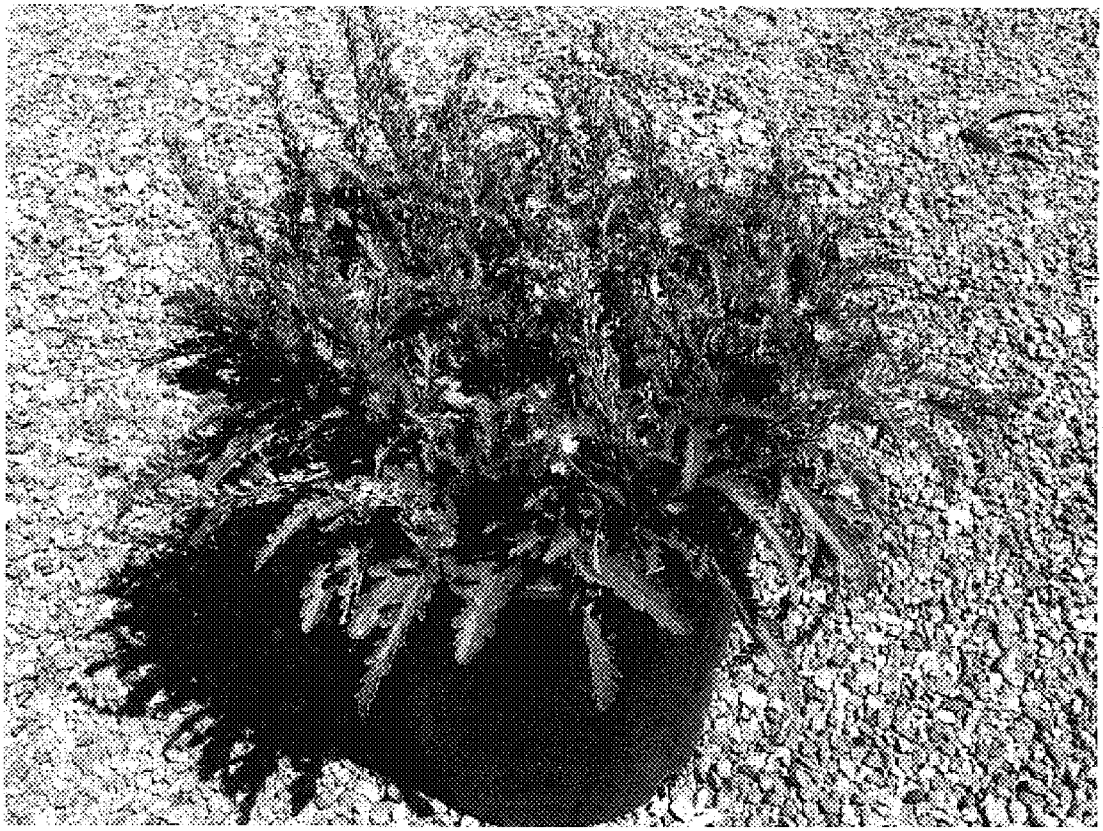
FIG. 1 depicts a one year old plant in a 1 liter container out of doors in Arroyo Grande, Calif.
Figure 2:
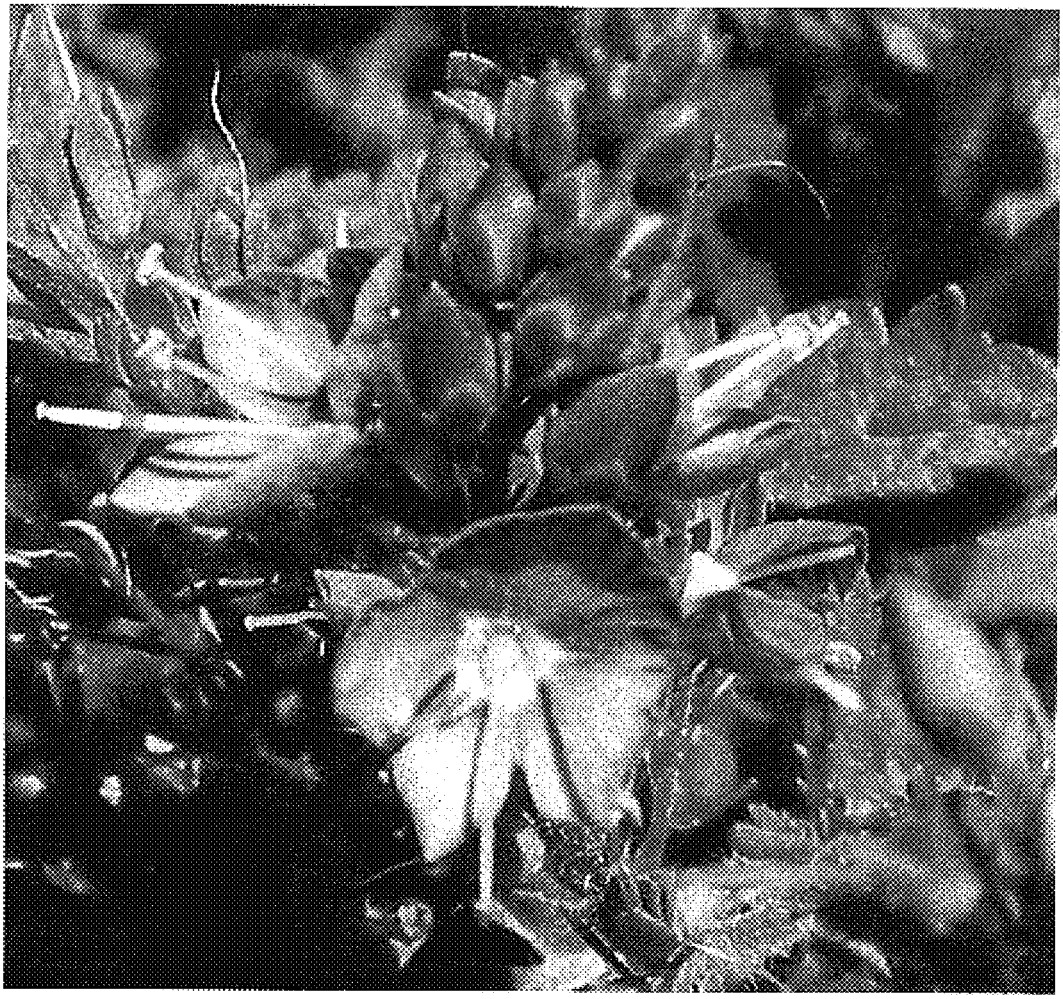
FIG. 2 is a close up of the inflorescence.
Figure 3:
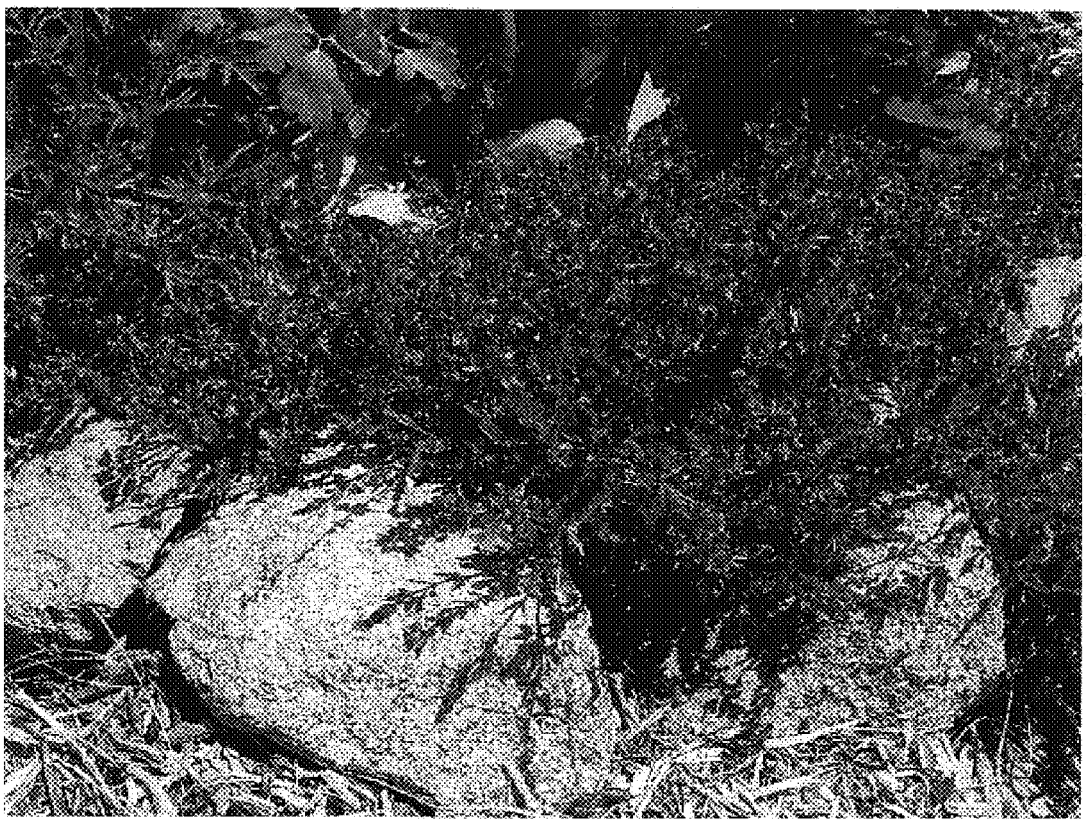
FIG. 3 depicts a mature plant approximately 3 years old in the inventor's garden in Newport, Wash.

Color in the drawings may differ from color values cited in the detailed botanical description, which accurately describe the actual color of the new *Veronica* variety named 'CHRISTY'. Drawings labeled FIG. 1, FIG. 2 and FIG. 3 were made using conventional techniques and although foliage colors may appear different from actual colors due to light reflectance, they are as accurate as possible by conventional photography.

BOTANICAL DESCRIPTION OF THE PLANT

The following is a detailed description of the new *Veronica* cultivar named 'CHRISTY'. Data was collected in Arroyo Grande, Calif. from 1 year old plants grown in 1-liter containers. Phenotypic differences may be observed with variations in environmental, climatic, and cultural conditions, without however, any difference in genotype. Color determinations are in accordance with the 2001 Royal Horticultural Society Color Chart except where general color terms of ordinary dictionary significance are used. The growing requirements are similar to the species.

Botanical classification: *Veronica×hybrida* 'CHRISTY'.
Family: Scrophulariaceae.
Genus: *Veronica*.
Species: *×hybrida*.
Denomination: 'CHRISTY'.
Common name: Speedwell.
Plant type: Herbaceous perennial.
Plant use: Border, rock garden, and as a groundcover for the landscape.
Plant parentage: *Veronica×hybrida* 'CHRISTY' is a seedling selection arising from the deliberate cross-pollination of the following parents:
- *Female parent.*—An individual *Veronica austriaca* 'Crater Lake Blue'.
- *Male parent.*—An unnamed individual *Veronica prostrata*.

Plant vigour: Moderate.
Branching habit: Basal branching.
Dimensions at maturity: 20 cm. in height and 40 cm. in width.
Plant hardiness: USDA Zone 3.
Asexual propagation method: Softwood cuttings and division.
Growth habit: Low and spreading.
Root system: Fibrous.
Cultural requirements: Plants in well-draining soil, and full sun with adequate but not excess water.
Time to initiate roots: 2 weeks to develop roots on an initial cutting.
Crop time: 8–10 weeks from a rooted cutting to a finished commercial 1-liter container.
Seasonal interest: Flowers from late spring through summer.
Stem:
- *Stem shape.*—Cylindrical.
- *Stem surface.*—Villous.
- *Color of villi.*—155B.
- *Stem length.*—Average of 5 cm.
- *Stem diameter.*—2 mm.
- *Stem color.*—138B.
- *Internodal distance.*—Ranges from 1 cm. to 1.50 cm.

Foliage:
- *Leaf arrangement.*—Whorl.
- *Leaf division.*—Simple.
- *Leaf shape.*—Lanceolate.
- *Leaf apex.*—Rounded.
- *Leaf base.*—Cuneate.
- *Leaf attachment.*—Combination of sheathing and petiolate on an individual plant.
- *Petiole length.*—Ranges from 0.75 cm. to 4.50 cm.
- *Petiole width.*—Ranges from less than 1 mm. to 2 mm.
- *Petiole shape.*—Sulcate.
- *Petiole surface.*—Villous.
- *Petiole color.*—137D and 144C.
- *Leaf margin.*—Pinnatifid.
- *Leaf surface (adaxial and abaxial surfaces).*—Villous.
- *Villi color.*—155B.
- *Leaf surface appearance (abaxial surface).*—Matte.
- *Leaf surface appearance (abaxial surface).*—Semi-glossy.
- *Leaf length.*—Ranges from 2.25 cm. to 7 cm.
- *Leaf width.*—Ranges from 0.50 cm. to 3 cm.
- *Leaf color (adaxial surface).*—137A.
- *Leaf color (abaxial surface).*—138B.
- *Venation pattern.*—Pinnate.
- *Vein color (adaxial surface).*—137A.
- *Vein color (abaxial surface).*—138B.
- *Foliage fragrance.*—None observed.

Inflorescence:
- *Inflorescence type.*—Terminal raceme.
- *Inflorescence dimensions.*—7 cm. in length and 1 cm. in width.
- *Inflorescence quantity.*—Ranges from 45–50 per 1-liter container plant.
- *Blooming season.*—Late spring through summer.
- *Flower quantity.*—Ranges from 35–40 per inflorescence.
- *Flower shape.*—Funnelform.
- *Flower dimensions.*—1 cm. in diameter and 0.75 cm. in depth.
- *Corolla tube depth.*—Less than 1 mm.
- *Number of petals.*—4 in number.
- *Petal color (adaxial and abaxial surfaces).*—N88A and N88D.
- *Corolla tube color.*—N144D.
- *Petal length.*—Ranges from 4 mm. to 5 mm. per individual flower.
- *Petal width.*—Ranges from 3 mm. to 6 mm. per individual flower.
- *Petal shape.*—Reniform and obovate.
- *Petal apex.*—Obtuse and subacute.
- *Petal base.*—Cuneate.
- *Petal margin.*—Entire.
- *Petal surface (adaxial and abaxial surfaces).*—Glabrous.
- *Peduncle length.*—Average is 10 cm.
- *Peduncle width.*—2 mm. in width.
- *Peduncle color.*—144C.

*Peduncle shape.*—Cylindrical.
*Peduncle surface.*—Villous.
*Villi color.*—155B.
*Pedicel dimensions.*—3 mm. in length and less than 0.50 mm. in diameter.
*Pedicel color.*—144C.
*Pedicel surface.*—Villous.
*Pedicel shape.*—Cylindrical.
*Calyx shape.*—Stellular.
*Calyx diameter.*—6 mm.
*Calyx color.*—138B.
*Sepals.*—4 in number.
*Sepals fused or unfused.*—Unfused.
*Sepal dimensions.*—3 mm. in length and 1.75 mm. in width.
*Sepal shape.*—Ovate.
*Sepal margin.*—Entire.
*Sepal color* (*adaxial and abaxial surfaces*).—138B.
*Sepal apex.*—Acute.
*Sepal surface.*—Villous.
*Bud dimensions.*—5 mm in length and 3.75 mm in diameter.
*Bud color.*—84D.
*Bud shape.*—Ovoid.
*Bud surface.*—Villous.
*Bud apex.*—Acute.
*Flower fragrance.*—None observed.
Reproductive organs:
*Stamens.*—2 in number.
*Stamen length.*—8 mm.
*Stamen color.*—155B.
*Anther dimensions.*—1 mm. in height and less than 0.50 mm. in width.
*Anther color.*—152C and 152D.
*Pistil.*—1 in number.
*Pistil length.*—7 mm.
*Pistil color.*—155B.
*Stigma shape.*—Rounded.
*Stigma surface.*—Glossy.
*Stigma color.*—155B.
*Stigma height.*—Less than 0.50 mm.
*Ovary shape.*—Globose.
*Ovary dimensions.*—Less than 1 mm in diameter and less than 1 mm. in height.
*Ovary color.*—145B.
*Ovary position.*—Superior.
Seed: No seed observed to date.

It is claimed:

1. A new and distinct variety of *Veronica* plant named 'CHRISTY' as described and illustrated herein.

* * * * *